United States Patent
Burg et al.

(10) Patent No.: US 9,226,800 B2
(45) Date of Patent: Jan. 5, 2016

(54) NAVIGATED MALLEABLE SURGICAL INSTRUMENT

(75) Inventors: Bruce M. Burg, Louisville, CO (US); Ross Smetzer, Valley Springs, CA (US); Andrew Bzostek, Erie, CO (US); Steven L. Hartmann, Superior, CO (US); Brad Jacobsen, Erie, CO (US); Matthew J. Nadeau, Lafayette, CO (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 678 days.

(21) Appl. No.: 13/097,243

(22) Filed: Apr. 29, 2011

(65) Prior Publication Data

US 2011/0270081 A1 Nov. 3, 2011

Related U.S. Application Data

(60) Provisional application No. 61/330,024, filed on Apr. 30, 2010.

(51) Int. Cl.
*A61B 5/06* (2006.01)
*A61B 17/24* (2006.01)
(Continued)

(52) U.S. Cl.
CPC ............ *A61B 19/5244* (2013.01); *A61B 17/24* (2013.01); *A61B 2017/00946* (2013.01);
(Continued)

(58) Field of Classification Search
CPC .................. A61B 19/5244; A61B 2019/5251; A61B 2019/5483; A61B 2019/547; A61B 2019/5475; A61B 17/24; A61B 2017/00946; A61M 2205/3576; A61M 2205/3561; A61M 1/008
USPC ........................................................ 600/424
See application file for complete search history.

(56) References Cited

U.S. PATENT DOCUMENTS 4,317,078 A 2/1982 Weed et al.
4,788,987 A 12/1988 Nickel
(Continued)

FOREIGN PATENT DOCUMENTS

AU 2011245296 A1 12/2012
CA 2797359 A1 11/2011
(Continued)

OTHER PUBLICATIONS

"Mayfield® Skull Clamps and Headrest Systems," Mayfield® Surgical Devices Product Index, pp. 1-6, Dec. 2004 Integra LifeSciences Corporation.
(Continued)

*Primary Examiner* — Long V Le
*Assistant Examiner* — Angela M Hoffa
(74) *Attorney, Agent, or Firm* — Harness, Dickey

(57) ABSTRACT

A surgical instrument can include a body, a tracking device, and a handle. The body can include proximal and distal ends, and a flow passage extending therebetween. The body can be formed from a malleable material such that it can be bent between the proximal and distal ends from a first configuration to a second bent configuration and maintain the bent configuration. The tracking device can be positioned adjacent the distal end for tracking a distal tip of the instrument. The handle can be coupled to the proximal end of the body and can include an internal flow passage in fluid communication with the body flow passage. The tracking device can include a pair of lead wires wound around the body to the handle, where the wound wires can conform to the bent configuration of the body such that they do not strain or break during bending of the body.

35 Claims, 7 Drawing Sheets

(51) Int. Cl.
  *A61B 19/00*     (2006.01)
  *A61B 17/00*     (2006.01)
  *A61M 1/00*      (2006.01)

(52) U.S. Cl.
  CPC .. *A61B 2019/5251* (2013.01); *A61B 2019/547* (2013.01); *A61B 2019/5475* (2013.01); *A61B 2019/5483* (2013.01); *A61M 1/008* (2013.01); *A61M 2205/3561* (2013.01); *A61M 2205/3576* (2013.01)

(56) References Cited

U.S. PATENT DOCUMENTS

| | | | |
|---|---|---|---|
| 4,806,182 A | 2/1989 | Rydell et al. | |
| 5,005,592 A * | 4/1991 | Cartmell | 128/899 |
| 5,226,423 A | 7/1993 | Tenerz et al. | |
| 5,391,199 A | 2/1995 | Ben-Haim | |
| 5,443,489 A | 8/1995 | Ben-Haim | |
| 5,591,141 A | 1/1997 | Nettekoven | |
| 5,592,939 A | 1/1997 | Martinelli | |
| 5,740,808 A | 4/1998 | Panescu et al. | |
| 5,762,637 A | 6/1998 | Berg et al. | |
| 5,840,024 A | 11/1998 | Taniguchi et al. | |
| 5,913,820 A | 6/1999 | Bladen et al. | |
| 5,938,602 A | 8/1999 | Lloyd | |
| 5,963,120 A | 10/1999 | Zaviska | |
| 5,983,126 A | 11/1999 | Wittkampf | |
| 6,021,343 A | 2/2000 | Foley et al. | |
| 6,106,486 A | 8/2000 | Tenerz et al. | |
| 6,201,387 B1 | 3/2001 | Govari | |
| 6,235,038 B1 | 5/2001 | Hunter et al. | |
| 6,253,770 B1 | 7/2001 | Acker et al. | |
| 6,254,600 B1 | 7/2001 | Willink et al. | |
| 6,332,891 B1 | 12/2001 | Himes | |
| 6,336,906 B1 | 1/2002 | Hammarstrom et al. | |
| 6,348,058 B1 | 2/2002 | Melkent et al. | |
| 6,381,485 B1 | 4/2002 | Hunter et al. | |
| 6,427,079 B1 | 7/2002 | Schneider et al. | |
| 6,434,507 B1 | 8/2002 | Clayton et al. | |
| 6,474,341 B1 | 11/2002 | Hunter et al. | |
| 6,478,802 B2 | 11/2002 | Kienzle, III et al. | |
| 6,556,857 B1 | 4/2003 | Estes et al. | |
| 6,610,066 B2 | 8/2003 | Dinger et al. | |
| 6,615,155 B2 * | 9/2003 | Gilboa | 702/150 |
| 6,616,651 B1 * | 9/2003 | Stevens | 604/524 |
| 6,687,531 B1 | 2/2004 | Ferre et al. | |
| 6,689,049 B1 * | 2/2004 | Miyagi et al. | 600/117 |
| 6,695,764 B2 | 2/2004 | Silverman et al. | |
| 6,747,539 B1 | 6/2004 | Martinelli | |
| 6,796,988 B2 | 9/2004 | Melkent et al. | |
| 6,833,814 B2 | 12/2004 | Gilboa et al. | |
| 6,926,674 B2 | 8/2005 | Tenerz et al. | |
| 6,940,941 B2 | 9/2005 | Gregerson et al. | |
| 6,977,575 B2 | 12/2005 | Bernier | |
| 6,980,849 B2 | 12/2005 | Sasso | |
| 6,993,374 B2 | 1/2006 | Sasso | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,118,378 B1 | 10/2006 | Karapetyan | |
| 7,166,114 B2 | 1/2007 | Moctezuma De La Barrera et al. | |
| 7,188,998 B2 | 3/2007 | Gregerson et al. | |
| 7,226,456 B2 | 6/2007 | O'Neil et al. | |
| 7,346,417 B2 | 3/2008 | Luth et al. | |
| 7,366,562 B2 | 4/2008 | Dukesherer et al. | |
| 7,410,480 B2 | 8/2008 | Muni et al. | |
| 7,462,175 B2 | 12/2008 | Chang et al. | |
| 7,500,971 B2 | 3/2009 | Chang et al. | |
| 7,537,594 B2 | 5/2009 | Sartor | |
| 7,559,137 B2 * | 7/2009 | Beer et al. | 29/825 |
| 7,604,609 B2 | 10/2009 | Jervis | |
| 7,625,617 B1 * | 12/2009 | Anderson et al. | 428/36.9 |
| 7,629,015 B2 * | 12/2009 | Anderson et al. | 427/2.1 |
| 7,637,896 B2 | 12/2009 | Voegele et al. | |
| 7,647,083 B2 | 1/2010 | Al-Ali et al. | |
| 7,697,972 B2 * | 4/2010 | Verard et al. | 600/424 |
| 7,751,865 B2 | 7/2010 | Jascob et al. | |
| 7,763,035 B2 | 7/2010 | Melkent et al. | |
| 7,774,933 B2 * | 8/2010 | Wilson et al. | 29/854 |
| 7,797,032 B2 | 9/2010 | Martinelli et al. | |
| 7,818,044 B2 * | 10/2010 | Dukesherer et al. | 600/424 |
| 7,840,253 B2 * | 11/2010 | Tremblay et al. | 600/424 |
| 7,844,319 B2 | 11/2010 | Susil et al. | |
| 7,971,341 B2 | 7/2011 | Dukesherer et al. | |
| 7,979,032 B2 | 7/2011 | Lomnitz | |
| 8,075,969 B2 * | 12/2011 | Anderson et al. | 428/36.9 |
| 8,086,298 B2 | 12/2011 | Whitmore, III et al. | |
| 8,105,339 B2 | 1/2012 | Melkent et al. | |
| 8,147,486 B2 | 4/2012 | Honour et al. | |
| 8,239,001 B2 * | 8/2012 | Verard et al. | 600/424 |
| 8,251,949 B2 * | 8/2012 | Warnack | 604/103.01 |
| 8,255,027 B2 | 8/2012 | Al-Ali et al. | |
| 8,504,139 B2 * | 8/2013 | Jacobsen et al. | 600/424 |
| 8,644,907 B2 | 2/2014 | Hartmann et al. | |
| 8,648,605 B2 | 2/2014 | Nakamura et al. | |
| 8,674,694 B2 | 3/2014 | Hyde et al. | |
| 8,862,204 B2 | 10/2014 | Sobe et al. | |
| 2001/0034549 A1 | 10/2001 | Bartholf et al. | |
| 2002/0165448 A1 | 11/2002 | Ben-Haim et al. | |
| 2003/0050552 A1 | 3/2003 | Vu | |
| 2003/0187347 A1 | 10/2003 | Nevo et al. | |
| 2004/0116803 A1 | 6/2004 | Jascob et al. | |
| 2004/0199072 A1 | 10/2004 | Sprouse et al. | |
| 2004/0215071 A1 | 10/2004 | Frank et al. | |
| 2005/0027339 A1 * | 2/2005 | Schrom et al. | 607/116 |
| 2005/0027340 A1 * | 2/2005 | Schrom et al. | 607/116 |
| 2005/0027341 A1 * | 2/2005 | Schrom et al. | 607/116 |
| 2005/0060885 A1 | 3/2005 | Johnson et al. | |
| 2005/0085715 A1 | 4/2005 | Dukesherer et al. | |
| 2005/0085720 A1 | 4/2005 | Jascob et al. | |
| 2005/0105212 A1 | 5/2005 | Sato | |
| 2005/0154294 A1 | 7/2005 | Uchiyama et al. | |
| 2005/0171508 A1 | 8/2005 | Gilboa | |
| 2005/0215922 A1 | 9/2005 | Tsonton et al. | |
| 2005/0222554 A1 | 10/2005 | Wallace et al. | |
| 2006/0004286 A1 | 1/2006 | Chang et al. | |
| 2006/0025677 A1 | 2/2006 | Verard et al. | |
| 2006/0036189 A1 | 2/2006 | Martinelli et al. | |
| 2006/0084867 A1 | 4/2006 | Tremblay et al. | |
| 2006/0142656 A1 | 6/2006 | Malackowski et al. | |
| 2006/0206039 A1 * | 9/2006 | Wilson et al. | 601/2 |
| 2006/0206170 A1 | 9/2006 | Denker et al. | |
| 2006/0224142 A1 * | 10/2006 | Wilson et al. | 604/510 |
| 2006/0229624 A1 | 10/2006 | May et al. | |
| 2006/0235314 A1 * | 10/2006 | Migliuolo et al. | 600/505 |
| 2007/0088416 A1 | 4/2007 | Atalar et al. | |
| 2007/0157828 A1 | 7/2007 | Susel et al. | |
| 2007/0197899 A1 | 8/2007 | Ritter et al. | |
| 2007/0208252 A1 * | 9/2007 | Makower | 600/424 |
| 2007/0220746 A1 * | 9/2007 | Anderson et al. | 29/885 |
| 2007/0225595 A1 | 9/2007 | Malackowski et al. | |
| 2007/0255132 A1 | 11/2007 | Shalgi et al. | |
| 2008/0097195 A1 | 4/2008 | Urquhart et al. | |
| 2008/0097347 A1 | 4/2008 | Arvanaghi | |
| 2008/0119727 A1 | 5/2008 | Barbagli et al. | |
| 2008/0119919 A1 | 5/2008 | Atalar et al. | |
| 2008/0132909 A1 | 6/2008 | Jascob et al. | |
| 2008/0171934 A1 | 7/2008 | Greenan et al. | |
| 2008/0171937 A1 | 7/2008 | Dukesherer et al. | |
| 2008/0172069 A1 | 7/2008 | Dukesherer et al. | |
| 2008/0228195 A1 | 9/2008 | von Jako et al. | |
| 2009/0088728 A1 | 4/2009 | Dollar et al. | |
| 2009/0118742 A1 | 5/2009 | Hartmann et al. | |
| 2009/0171187 A1 | 7/2009 | Gerhart et al. | |
| 2009/0204023 A1 | 8/2009 | Goldenberg | |
| 2009/0209947 A1 | 8/2009 | Gordin et al. | |
| 2010/0063383 A1 | 3/2010 | Anderson et al. | |
| 2010/0081965 A1 | 4/2010 | Mugan et al. | |
| 2010/0130852 A1 * | 5/2010 | Neidert et al. | 600/424 |
| 2010/0185083 A1 * | 7/2010 | Neidert et al. | 600/424 |
| 2010/0210939 A1 | 8/2010 | Hartmann et al. | |
| 2010/0228117 A1 | 9/2010 | Hartmann | |
| 2010/0234724 A1 | 9/2010 | Jacobsen et al. | |
| 2010/0253361 A1 | 10/2010 | Nakamura et al. | |

(56) References Cited

U.S. PATENT DOCUMENTS

| | | | |
|---|---|---|---|
| 2010/0280363 A1* | 11/2010 | Skarda et al. | 600/424 |
| 2010/0331763 A1* | 12/2010 | Wilson et al. | 604/22 |
| 2011/0014705 A1 | 1/2011 | Leach et al. | |
| 2011/0060214 A1* | 3/2011 | Makower | 600/424 |
| 2011/0066029 A1* | 3/2011 | Lyu et al. | 600/424 |
| 2011/0118592 A1 | 5/2011 | Sobe et al. | |
| 2011/0251519 A1* | 10/2011 | Romoscanu | 600/585 |
| 2011/0258842 A1 | 10/2011 | Dukesherer et al. | |
| 2012/0172696 A1 | 7/2012 | Kallback et al. | |
| 2012/0197108 A1 | 8/2012 | Hartmann et al. | |
| 2012/0197109 A1 | 8/2012 | Hartmann et al. | |
| 2012/0197110 A1 | 8/2012 | Hartmann et al. | |
| 2012/0245665 A1* | 9/2012 | Friedman et al. | 607/127 |
| 2012/0283570 A1 | 11/2012 | Tegg | |
| 2013/0066194 A1 | 3/2013 | Seter et al. | |
| 2013/0137954 A1* | 5/2013 | Jacobsen et al. | 600/373 |
| 2013/0317355 A1* | 11/2013 | Jacobsen et al. | 600/424 |
| 2014/0012130 A1* | 1/2014 | Jacobsen et al. | 600/424 |
| 2014/0148692 A1 | 5/2014 | Hartmann et al. | |
| 2014/0158555 A1 | 6/2014 | Nakamura et al. | |
| 2014/0276004 A1 | 9/2014 | Strupeck et al. | |
| 2015/0005625 A1 | 1/2015 | Sobe et al. | |

FOREIGN PATENT DOCUMENTS

| | | |
|---|---|---|
| DE | 102009030731 A1 | 12/2010 |
| EP | 0425319 A2 | 5/1991 |
| EP | 1302172 A1 | 4/2003 |
| EP | 1552795 A1 | 7/2005 |
| EP | 1658818 A1 | 5/2006 |
| EP | 1743591 A2 | 1/2007 |
| EP | 1806756 A2 | 7/2007 |
| EP | 2123220 A1 | 11/2009 |
| EP | 2563260 A2 | 3/2013 |
| JP | 03-207344 B2 | 9/2001 |
| JP | 2007-527296 A | 9/2007 |
| JP | 2008194475 A | 8/2008 |
| JP | 2010082446 A | 4/2010 |
| WO | WO-9632060 A1 | 10/1996 |
| WO | WO-9729682 A1 | 8/1997 |
| WO | WO-9729684 A1 | 8/1997 |
| WO | WO-9940856 A1 | 8/1999 |
| WO | WO-0038571 A1 | 7/2000 |
| WO | WO-2006096685 A1 | 9/2006 |
| WO | WO-2006116597 A2 | 11/2006 |
| WO | WO-2008105874 A1 | 9/2008 |
| WO | WO-2009152486 A1 | 12/2009 |
| WO | WO-2010049834 A1 | 5/2010 |
| WO | WO-2010124285 A1 | 10/2010 |
| WO | WO-2010144419 A2 | 12/2010 |
| WO | WO-2011137301 A2 | 11/2011 |
| WO | WO-2012103304 A1 | 8/2012 |
| WO | WO-2012103407 A1 | 8/2012 |
| WO | WO-2012103410 A1 | 8/2012 |
| WO | WO-2013062869 A1 | 5/2013 |

OTHER PUBLICATIONS

"Medtronic O-Arm Multi-Dimensional Surgical Imaging System"; Brochure, 24pp, 2009.

"StealthStation_S7_System® Information Center in the OR," (2009) Medtronic, Inc.

"StealthStation® Tria™ plus Treatment Guidance System," brochure, Medtronic Surgical Navigation Technologies (2004) 2 pages.

"Treon, StealthStation," brochure, Medtronic Surgical Navigation Technologies (2001) 8 pages.

International Preliminary Report on Patentability mailed Nov. 15, 2012 for PCT/US2011/34475 claiming benefit of U.S. Appl. No. 13/097,243, filed Apr. 29, 2011.

International Search Report and Written Opinion mailed Feb. 6, 2013 for PCT/US2012/061086 claiming benefit of U.S. Appl. No. 13/281,001, filed Oct. 25, 2011.

International Search Report and Written Opinion mailed Jul. 6, 2012 for PCT/US2012/022840 claiming benefit to U.S. Appl. No. 13/016,762, filed Jan. 28, 2011.

International Search Report and Written Opinion mailed May 9, 2012 for PCT/US2012/022676 claiming benefit of U.S. Appl. No. 13/016,740, filed Jan. 28, 2011.

International Search Report and Written Opinion mailed May 9, 2012 for PCT/US2012/022846 claiming benefit of U.S. Appl. No. 13/016,765, filed Jan. 28, 2011.

Invitation to Pay Additional Fees mailed Dec. 17, 2012 for PCT/US2012/061086 claiming benefit of U.S. Appl. No. 13/281,001, filed Oct. 25, 2011.

Invitation to Pay Additional Fees mailed May 8, 2012 for PCT/US2012/022840 claiming benefit of U.S. Appl. No. 13/016,762, filed Jan. 28, 2011.

Medtronic Navigation, "StealthStation® Axiem™ Electromagnetic Navigation . . . ", 2005, www.stealthstation.com/physician/spine/library/axiem_ent.jsp, printed Aug. 19, 2006 (2 pages).

"InstaTrak 3500 Plus. Applications: ENT. Cranial." http://www.gehealthcare/usen/xr/surgery/products/nav.html (printed Dec. 14, 2009).

"InstaTrak® Image Guided Sinus Surgery, Introduction to the InstaTrak System." Sinus-Clear.com http:/www.sinus-clear.com/instatrak.htm (printed Dec. 14, 2009).

"InstaTrak™ 3500 plus—Cranial. Multi-application electromagnetic surgical navigation system for ENT, Cranial, and Spine procedures." GE Healthcare http://www.gehealthcare.com/euen/surgery/products/instatrak-3500-plus-cranial/index.html (printed Dec. 14, 2009).

"InstaTrak™ 3500 plus—ENT. Multi-application electromagnetic surgical navigation system for ENT and Cranial." GE Healthcare http://www.gehealthcare.com/euen/surgery/products/instatrak-3500-plus-ent/index.html (printed Dec. 14, 2009).

"The doctor can see you now" brochure. GE Medical Systems (2003) General Electric Company.

Acclarent™ "Instructions for Use. Balloon Sinuplasty™ System. Relieva™ Devices, ReliENT™ Navigation System, and OptiLINK™ Extension." (Aug. 21, 2009) pp. 1-13.

Acclarent™ "Instructions for Use. Relieva Flex™ Sinus Guide Catheter, Relieva® Sinus Guide Catheter." (Sep. 19, 2009) pp. 1-6.

International Search Report and Written Opinion mailed Oct. 31, 2011, claiming benefit of U.S. Appl. No. 13/097,243, filed Apr. 29, 2011.

Invitation to Pay Additional Fees mailed Jul. 25, 2011, claiming benefit of U.S. Appl. No. 13/097,243, filed Apr. 29, 2011.

"Flexible electronics," Dec. 19, 2012, XP055112518, en.wikipedia.org. Retrieved form the Internet: <URL:http://en.wikipedia.org/w/index.php?title=Flexible_electronics&oldid=528841651> [retrieved on Apr. 7, 2014]. (6 sheets).

"Flexible Printed Circuit Manufacturer—Capabilities," Aug. 16, 2012, XP055112534, fpcexpress.com. Retrieved from the Internet: URL: <http://web.archive.org/web/20120816030431/http://fpcexpress.com/capabilities.html>. [retrieved on Apr. 7, 2014][retrieved on May 8, 2014]. (3 sheets).

"Minco Bulletin FC-3," Jul. 31, 2002. XP055115671, Retrieved from the Internet: <URL:http://www.temflexcontrols.com/pdf/fc3.pdf> [retrieved on Apr. 29, 2014]. (1 sheet).

"Sectional design standard for flexible printed boards," Internet Citation, Nov. 30, 1998, pp. 1-35, XP002691487, Retrieved form the Interent: <URL:http://222.184.16.210/smt/tzxt/bz/IPC-2223.pdf>. [retrieved on Feb. 1, 2013].

International Preliminary Report on Patentability and Written Opinion mailed May 8, 2014 for PCT/US2012/061086 claiming benefit of U.S. Appl. No. 13/281,001, filed Oct. 25, 2011.

International Search Report and Written Opinion mailed Apr. 23, 2014 for PCT/US2014/012786 claiming benefit of U.S. Appl. No. 13/748,150, filed Jan. 23, 2013.

International Search Report and Written Opinion mailed May 12, 2014 for PCT/US2014/012967 claiming benefit of U.S. Appl. No. 13/751,032, filed Jan. 25, 2013.

http://oxforddictionaries.com/definition/english/barrel (accessed Dec. 3, 2012).

(56) References Cited

OTHER PUBLICATIONS

International Preliminary Report on Patentability mailed Aug. 8, 2013 for PCT/US2012/022676 claiming benefit of U.S. Appl. No. 13/016,740, filed Jan. 28, 2011.

International Preliminary Report on Patentability mailed Aug. 8, 2013 for PCT/US2012/022840 claiming benefit of U.S. Appl. No. 13/016,762, filed Jan. 28, 2011.

International Preliminary Report on Patentability mailed Aug. 8, 2013 for PCT/US2012/022846 claiming benefit of U.S. Appl. No. 13/016,765, filed Jan. 28, 2011.

Examiner's Report dated Dec. 18, 2013 for Canadian Application No. 2,797,359 claiming benefit of U.S. Appl. No. 13/097,243, filed Apr. 29, 2011.

Japanese Office Action dated Jan. 7, 2014 for Japan Application No. 2013-508273 claiming benefit of U.S. Appl. No. 13/097,243, filed Apr. 29, 2011.

Chinese Office Action dated Sep. 3, 2014 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.

International Search Report and Written Opinion mailed Oct. 27, 2014 for PCT/US2014/028100 claiming benefit of U.S. Appl. No. 14/209,696, filed Mar. 13, 2014.

Invitation to Pay Additional Fees and Where Applicable, Protest Fee mailed Aug. 14, 2014 for PCT/US2014/028100 claiming benefit of U.S. Appl. No. 14/209,696 filed Mar. 13, 2014.

Chinese Office Action dated Apr. 3, 2015 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.

Communication pursuant to Article 94(3) EPC for European Application No. 12703208.4-1654 dated Apr. 24, 2015.

Internatiional Preliminary Report on Patentability and Written Opinion maile don Aug. 6, 2015 for PCT/US2014/012786 claiming benefit of U.S. Appl. No. 13/748,150, filed Jan. 23, 2013.

International Preliminary Report on Patentability and Written Opinion mailed on Aug. 6, 2015 for PCT/US2014/012967 claiming benefit of U.S. Appl. No. 13/751,032, filed Jan. 25, 2013.

International Preliminary Report on Patentability and Written Opinion mailed Sep. 24, 2015 for PCT/US2014/028100 claiming benefit to U.S. Appl. No. 14/209,696, filed Mar. 13, 2014.

International Preliminary Report on Patentability mailed Oct. 27, 2015 for PCT/US2014/034022 claiming benefit of U.S. Appl. No. 13/871,616, filed Apr. 26, 2013.

* cited by examiner

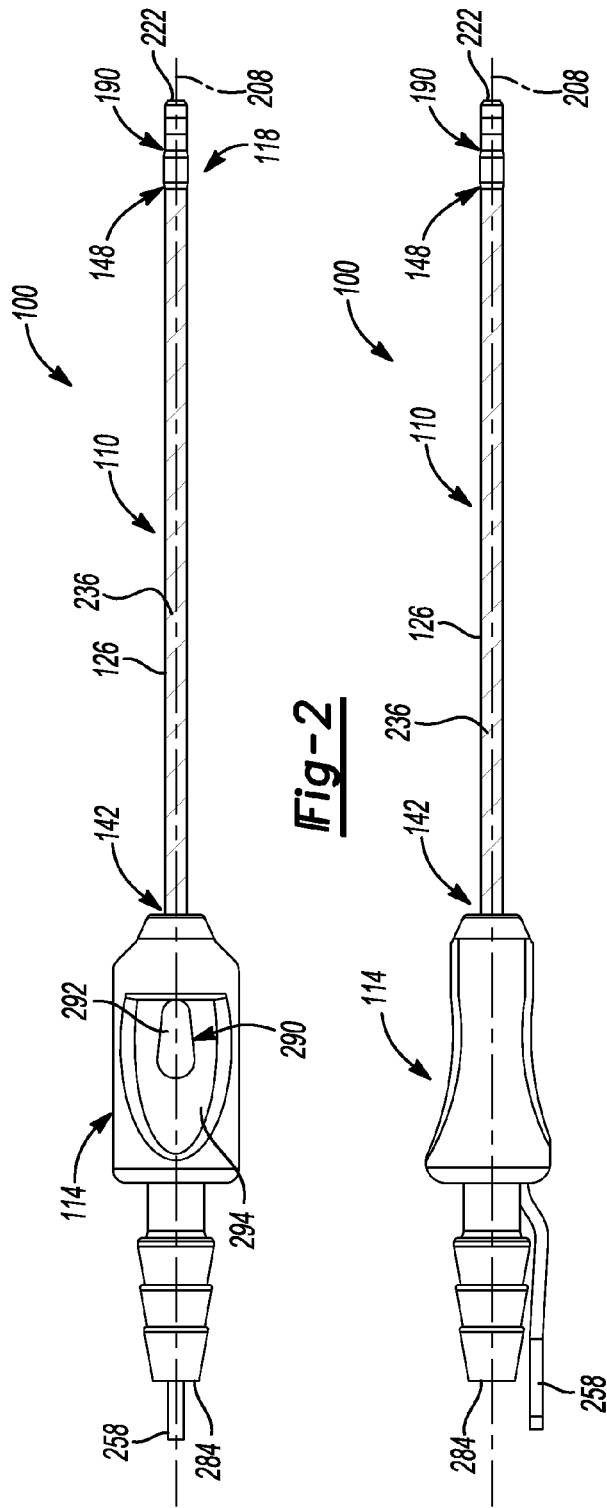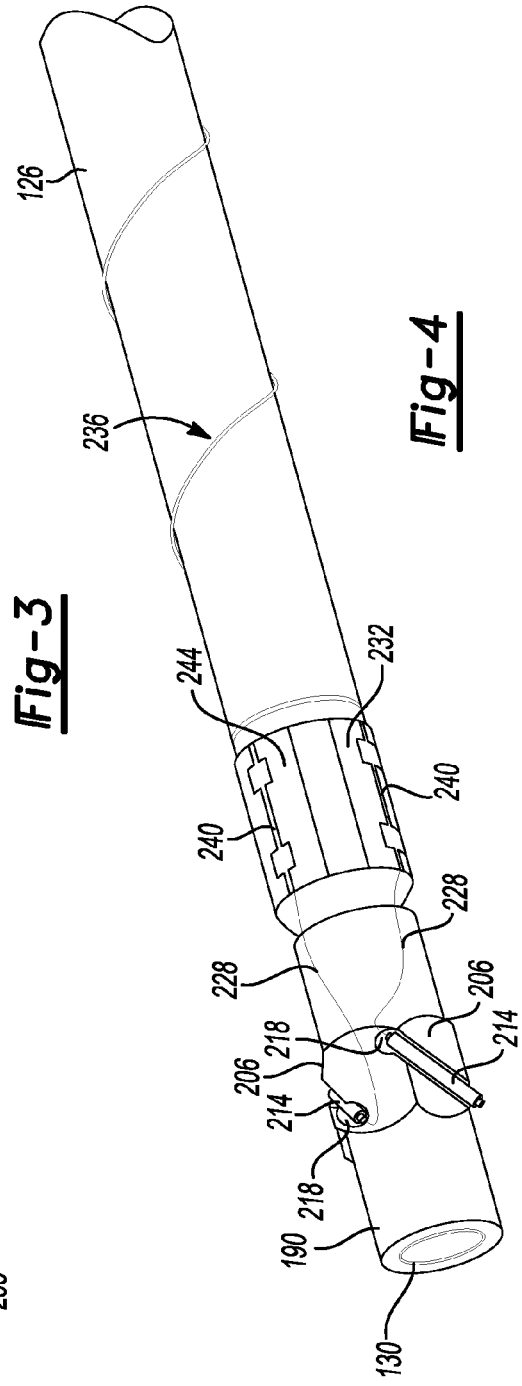

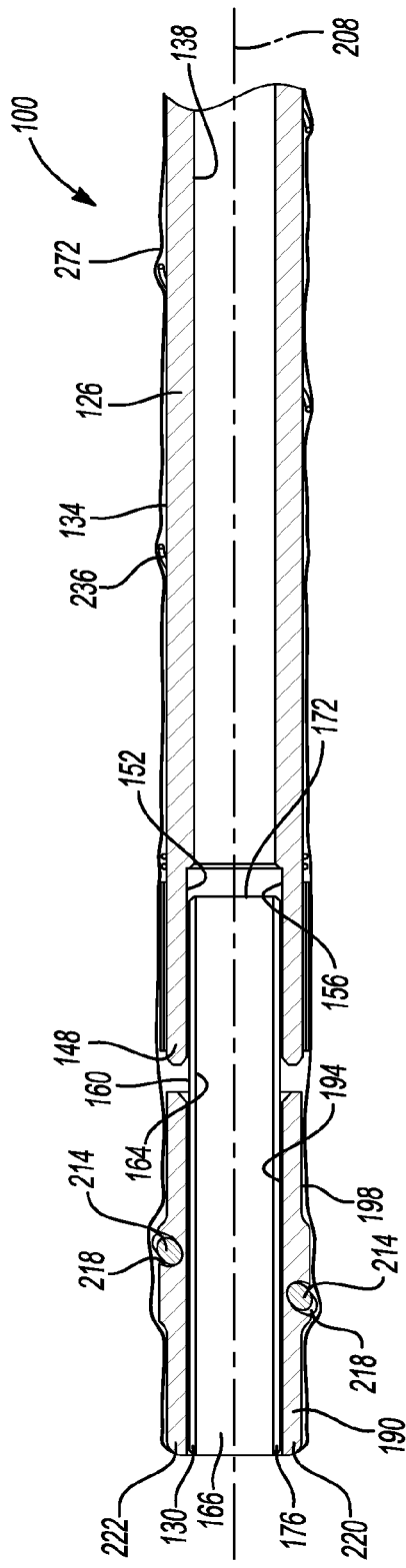
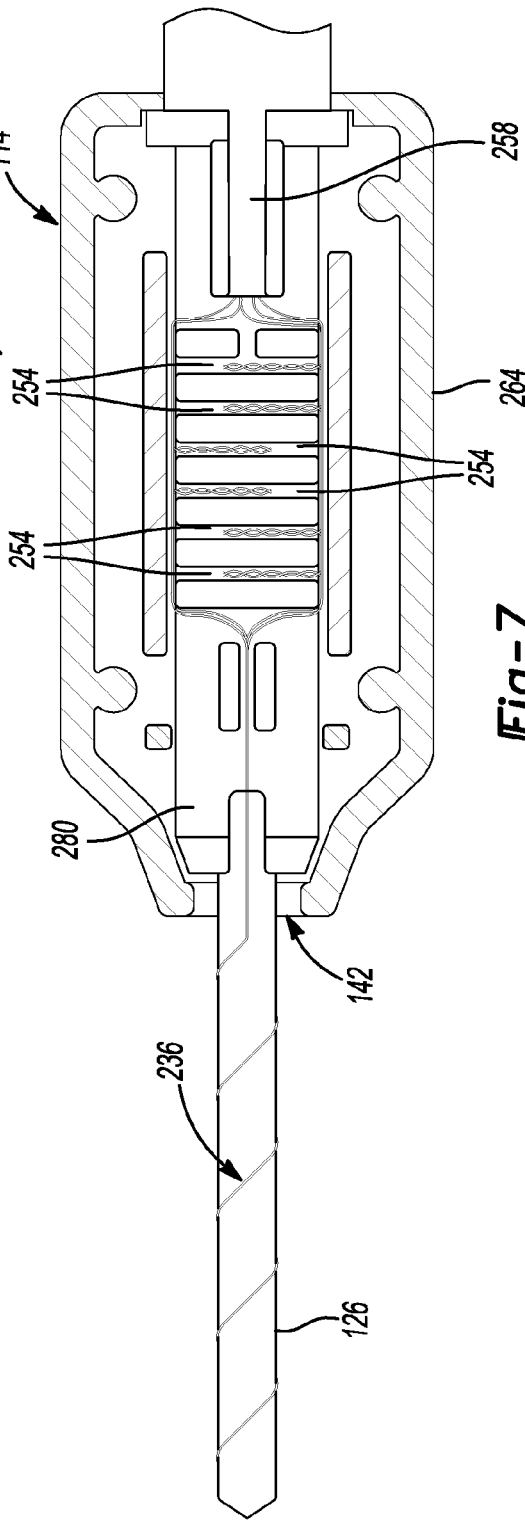

NAVIGATED MALLEABLE SURGICAL INSTRUMENT

CROSS-REFERENCE TO RELATED APPLICATIONS

This application claims the benefit of U.S. Provisional Patent Application No. 61/330,024 filed on Apr. 30, 2010. The disclosure of the above application is incorporated herein by reference.

FIELD

The present disclosure relates generally to a navigated malleable surgical instrument.

BACKGROUND

The statements in this section merely provide background information related to the present disclosure and may not constitute prior art.

Surgical procedures can be performed on anatomies such as the human anatomy for providing a therapy to the anatomy. One area of surgery includes procedures performed on facial cavities of a patient such as on the ear, nose or throat (ENT). In such a procedure, a surgical instrument such as a suction device may be inserted into such a cavity to perform a procedure for example. Because the viewing angle of a surgeon at the area of interest can be obscured by the surrounding tissue of the cavity, the ability of a surgeon to effectively apply a therapy, such as a suction procedure, can be reduced. Therefore, it is desirable to provide a mechanism so that a surgeon can provide a therapy without minimization or reduction of effectiveness of the procedure or in viewing the area to apply the therapy.

In navigation systems, instruments are provided with tracking devices. Sometimes, however, such tracking devices can be difficult to manipulate or cumbersome to the instrument. In other instances, the tracking devices can be positioned in a handle or proximal region of the instrument such that if the distal tip moves or is moved relative to the handle, the distal tip can no longer be accurately tracked.

In some procedures, it may also be difficult to effectively guide the surgical instrument through various shaped cavities of the anatomy. In an effort to address this difficulty, instruments have been developed that include flexible elongated portions configured to be permanently flexible. While these flexible instruments can conform to internal cavities of the anatomy, they do not retain any specific configuration, such that they are generally not suitable for certain procedures, such as an ENT suction procedure.

SUMMARY

This section provides a general summary of the disclosure, and is not a comprehensive disclosure of its full scope or all of its features.

In one form, a surgical instrument is provided and can include an elongated body portion, a tracking device, and a handle portion. The elongated body portion can include a proximal end, a distal end, and an inner diameter defining a first internal flow passage between the proximal and distal ends. The body portion can be formed from a malleable metallic material such that the body portion can be bent between the proximal and distal ends from a first configuration to a second bent configuration and maintain the bent configuration. The tracking device can be positioned adjacent or near the distal end and can be adapted to cooperate with a navigation system to track a distal tip of the instrument. The handle portion can be coupled to the proximal end of the body portion and can include a second internal flow passage in fluid communication with the first internal flow passage. The tracking device can include at least a pair of lead wires wound around the body portion from the tracking device to the handle portion, the wound lead wires can be configured to conform to the bent configuration of the body portion such that they do not strain or break during bending of the body portion.

In another form, a surgical instrument is provided and can include an elongated tubular body portion, a tubular insert portion, and a sleeve. The tubular body portion can have a proximal end, a distal end, and an inner diameter defining a first internal flow passage between the proximal and distal ends. The body portion can be formed from a malleable metallic material such that the body portion can be bent between the proximal and distal ends from a first configuration to a second bent configuration and maintain the bent configuration. The tubular insert portion can have a proximal end and a distal tip, the proximal end of the insert portion can be received in the inner diameter of the distal end of the body portion, and the insert portion can be formed of a rigid, non-bendable material. The sleeve can be configured to be received over the insert portion and extend from the distal end thereof partially towards the proximal end. The instrument can further include a tracking device and a handle portion. The tracking device can be coupled to the sleeve adjacent to the distal tip of the insert, and can be adapted to cooperate with a navigation system to track the distal tip of the instrument. The handle portion can be coupled to the proximal end of the body portion and can include a second internal flow passage in fluid communication with the first internal flow passage. The tracking device can include at least a pair of lead wires helically wound around the body portion at an acute angle relative to a longitudinal axis of the body portion, where the helically wound pair of lead wires can be configured to conform to the bent configuration of the body portion such that they do not strain or break during bending of the body portion. A flexible outer layer can cover the body portion, sleeve, insert and tracking device.

Further areas of applicability will become apparent from the description provided herein. It should be understood that the description and specific examples are intended for purposes of illustration only and are not intended to limit the scope of the present teachings.

BRIEF DESCRIPTION OF THE DRAWINGS

The present teachings will become more fully understood from the detailed description, the appended claims and the following drawings. The drawings are for illustrative purposes only and are not intended to limit the scope of the present disclosure.

FIG. 2 is a top plan view of an exemplary malleable suction instrument for use with the navigation system according to the principles of the present disclosure;

FIG. 3 is a side view of the exemplary suction instrument according to the principles of the present disclosure;

FIG. 4 is a partial perspective view of a distal region of the exemplary suction instrument according to the principles of the present disclosure;

FIG. 6 is a partial sectional view of the exemplary suction instrument of FIG. 5 according to the principles of the present disclosure;

FIG. 7 is a partial view of a handle portion of the exemplary suction instrument according to the principles of the present disclosure;

DETAILED DESCRIPTION OF THE VARIOUS EMBODIMENTS

Figure 1:
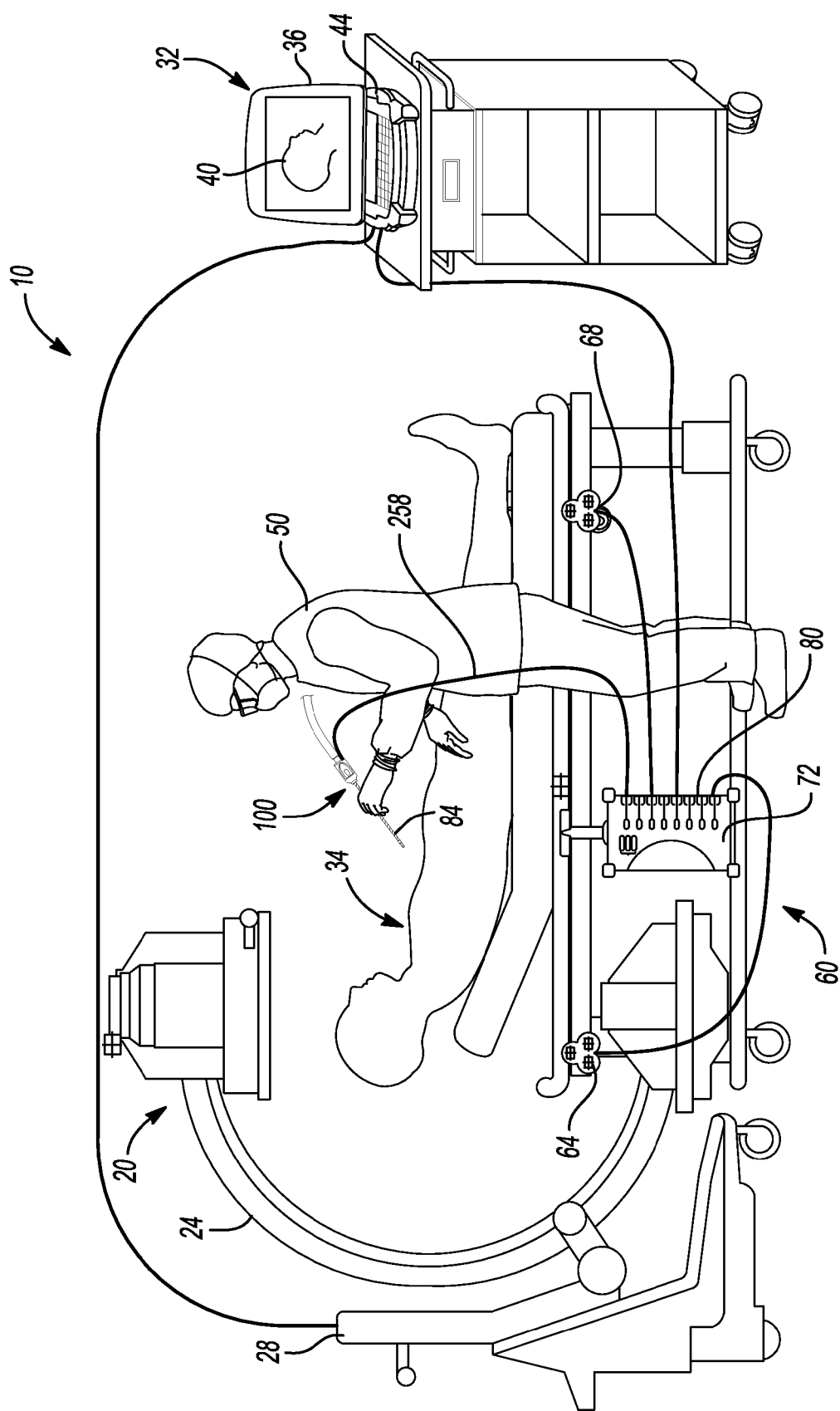
FIG. 1 is a perspective view of an exemplary navigation system according to the principles of the present disclosure.

The following description is merely exemplary in nature and is in no way intended to limit the present disclosure, its application, or uses. It should also be understood that throughout the drawings, corresponding reference numerals indicate like or corresponding parts and features.

FIG. 1 is a diagram schematically illustrating an overview of an image-guided navigation system 10 for use in the non-line-of-site navigating of a surgical instrument 100, such as a navigable malleable suction device or suction instrument, according to various exemplary embodiments of the present disclosure. Exemplary navigation systems include those disclosed in U.S. Pat. No. 7,366,562, issued on Apr. 29, 2008 to John H. Dukesherer et al. and U.S. Pat. App. Pub No. 2008/0132909, published Jun. 5, 2008, to Bradley A. Jascob et al., both incorporated herein by reference. Commercial navigation systems include the StealthStation® AxiEM™ Surgical Navigation System sold by Medtronic Navigation, Inc. having a place of business in Louisville, Colo., USA. It should be appreciated that while the navigation system 10 and suction instrument 100 are generally described in connection with an ear, nose and throat (ENT) procedure, navigation system 10 and suction instrument 100 can be used in various other appropriate procedures.

Generally, the navigation system 10 can be used to track a location of suction instrument 100, including a distal tip or end thereof, as will be described herein. Navigation system 10 can generally include an optional imaging system 20, such as a fluoroscopic X-ray imaging device configured as a C-arm 24 and an image device controller 28. The C-arm imaging system 20 can be any appropriate imaging system, such as a digital or CCD camera, which are well understood in the art. Image data obtained can be stored in the C-arm controller 28 and sent to a navigation computer and/or processor controller or work station 32 having a display device 36 to display image data 40 and a user interface 44. The work station 32 can also include or be connected to an image processor, navigation processor, and a memory to hold instruction and data. The work station 32 can include an optimization processor that assists in a navigated procedure. It will also be understood that the image data is not necessarily first retained in the controller 28, but may also be directly transmitted to the workstation 32. Moreover, processing for the navigation system and optimization can all be done with a single or multiple processors all of which may or may not be included in the work station 32.

The work station 32 provides facilities for displaying the image data 40 as an image on the display device 36, saving, digitally manipulating, or printing a hard copy image of the received image data. The user interface 44, which may be a keyboard, mouse, touch pen, touch screen or other suitable device, allows a physician or user 50 to provide inputs to control the imaging device 20, via the C-arm controller 28, or adjust the display settings of the display device 36.

With continuing reference to FIG. 1, the navigation system 10 can further include a tracking system, such as an electromagnetic (EM) tracking system 60. The discussion of the EM tracking system 60 can be understood to relate to any appropriate tracking system. The EM tracking system 60 can include a localizer, such as a coil array 64 and/or second coil array 68, a coil array controller 72, a navigation probe interface 80, and the trackable suction instrument 100. Instrument 100 can include an instrument tracking device or devices 84, as will be discussed herein. Briefly, the tracking device 84 can include an electromagnetic coil to sense a field produced by the localizing coil arrays 64, 68 and provide information to the navigation system 10 to determine a location of the tracking device 84. The navigation system 10 can then determine a position of a distal tip of the suction instrument 100 to allow for navigation relative to the patient 34 and patient space.

The EM tracking system 60 can use the coil arrays 64, 68 to create an electromagnetic field used for navigation. The coil arrays 64, 68 can include a plurality of coils that are each operable to generate distinct electromagnetic fields into the navigation region of the patient 34, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil arrays 64, 68 can be controlled or driven by the coil array controller 72. The coil array controller 72 can drive each coil in the coil arrays 64, 68 in a time division multiplex or a frequency division multiplex manner. In this regard, each coil may be driven separately at a distinct time or all of the coils may be driven simultaneously with each being driven by a different frequency.

Upon driving the coils in the coil arrays 64, 68 with the coil array controller 72, electromagnetic fields are generated within the patient 34 in the area where the medical procedure is being performed, which is again sometimes referred to as patient space. The electromagnetic fields generated in the patient space induce currents in the tracking device 84 positioned on or in the suction instrument 100. These induced signals from the tracking device 84 can be delivered to the navigation probe interface 80 and subsequently forwarded to the coil array controller 72. The navigation probe interface 80 can also include amplifiers, filters and buffers to directly interface with the tracking device 84 in the instrument 100. Alternatively, the tracking device 84, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 80.

The tracking system 60, if it is using an electromagnetic tracking assembly, essentially works by positioning the coil arrays 64, 68 adjacent to the patient 32 to generate a magnetic field, which can be low energy, and generally referred to as a navigation field. Because every point in the navigation field or patient space is associated with a unique field strength, the electromagnetic tracking system 60 can determine the position of the instrument 100 by measuring the field strength at the tracking device 84 location. The coil array controller 72 can receive the induced signals from the tracking device 84 and transmit information regarding a location, where location information can include both x, y, and z position and roll, pitch, and yaw orientation information, of the tracking device 84 associated with the tracked suction instrument 100. Accordingly, six degree of freedom (6 DOF) information can be determined with the navigation system 10.

Referring now to FIGS. 2-10, the navigated malleable surgical instrument 100 will be described in greater detail. In one exemplary configuration, the malleable surgical instrument 100 can be used for suction, including fluid and tissue removal in ENT procedures. It should be appreciated, however, that the navigated malleable surgical instrument 100 can be used in various other surgical procedures as may be desired and can be provided in the form of a malleable or flexible endoscope, a malleable or flexible catheter, and/or a malleable cannula. Thus, while the following description continues with reference to a navigated malleable suction instrument 100, the discussion is also applicable to the surgical instruments discussed above.

Suction instrument 100 can include a tube assembly 110, a handle assembly 114 and a tracking sensor arrangement 118. Suction instrument 100 can be configured for a single use such that it would be disposed after such use. The tube assembly 110 can include a malleable elongated tubular body 126 and an insert portion 130. The tubular body 126 can include an outer diameter 134 and an inner diameter 138 and can have a first end 142 coupled to the handle assembly 114 and a second opposite end 148 configured to receive insert portion 130, as shown in FIG. 6. The second end 148 can include an internal annular recess 152 having an inner diameter 156 greater than the inner diameter 138 of the remaining portion of body 126, as also shown in FIG. 6. The malleable elongated body 126 can be formed from various aluminum alloys, such as AL 3003-O, and various stainless steel alloys, such as 304 annealed, such that it is malleable to facilitate being bent or formed into various configurations and retaining the bent or formed configuration, as will be discussed herein. The body 126 can also be provided in various lengths and diameters, including 7, 9 and 12 French diameters.

The insert portion 130 can be configured to provide non-malleable support for at least the tracking sensor 84. Insert portion 130 can include an outer diameter 160 substantially equal to the inner diameter 156 of annular recess 152, and an inner diameter 164 substantially equal to the inner diameter 138 of malleable elongated body 126, as also shown in FIG. 6. In this manner, the substantially equal inner diameters 138, 164 can provide for a substantially constant flow path 166 for suction. It should be appreciated, however, that the inner diameters 138, 164 can also be provided with varying dimensions. Insert portion 130 can include a first end 172 and a second opposite end 176. The first end 172 of the insert portion 130 can be received in annular recess 152, as shown in FIG. 6. Insert portion can include a rigid construction to facilitate receiving and housing tracking device 84, as will be described herein. In this manner, insert portion 130 can be formed or manufactured from stainless steel or other biocompatible rigid materials such that insert portion 130 is not malleable like elongated body 126. The insert portion can also include an exemplary axial length of approximately 10 mm.

Figure 5:
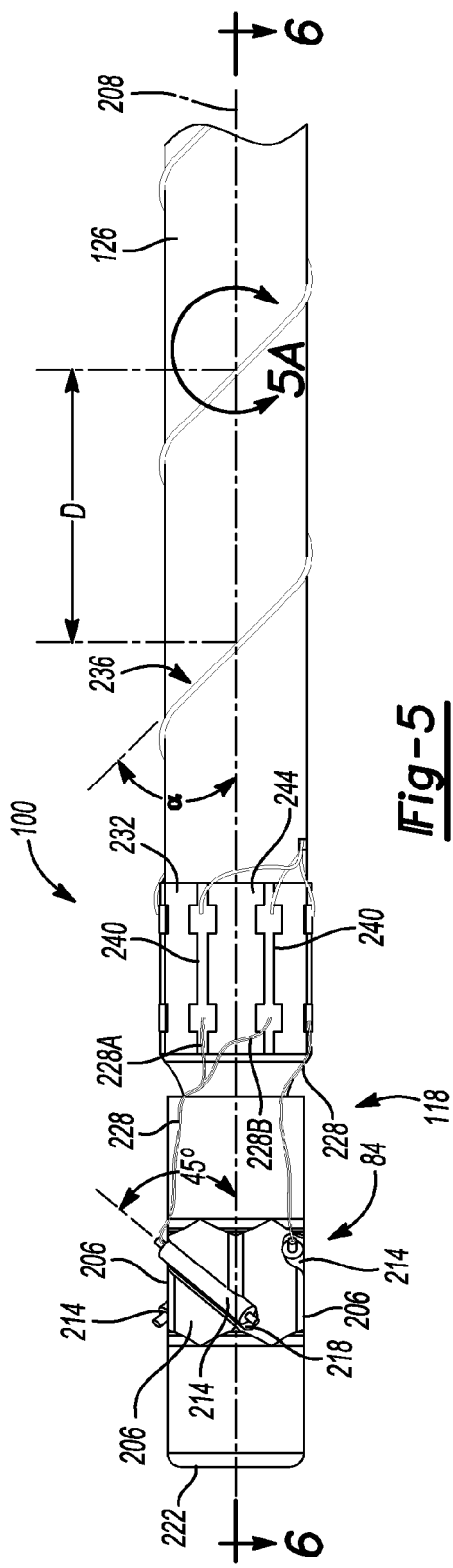
FIG. 5 is a partial side view of the distal region of the exemplary suction instrument according to the principles of the present disclosure.

Insert portion 130 can include a sleeve 190 received on an exterior thereof, as shown in FIGS. 5 and 6. Sleeve 190 can include an inner diameter 194 substantially equal to the outer diameter of insert portion 130, and an outer diameter 198 substantially equal to the outer diameter 134 of body 126. It should be appreciated that sleeve 190 can also be configured with different diameters relative to body 126. Sleeve 190 can extend over a portion of insert 130 from the first end 172 of the insert portion 130 towards the second end, as shown in FIG. 6. In one exemplary configuration, sleeve 190 can extend from the first end 172 and contact the first end 142 of body 126 when the insert portion 130 is coupled to annular recess 152 of body 126. In another exemplary configuration, sleeve 190 can extend from the first end 172 of body portion 130 in a similar manner as discussed above, but can stop short of the first end 142 of body 126, as shown in FIG. 6. Sleeve 190 can be fixed to insert portion 130, and insert portion 130 can be fixed to annular recess 152 with an appropriate adhesive. Sleeve 190 can be formed of a polymeric material or other suitable materials. Sleeve 190 can also include a first end 220 configured to substantially align with the second end 176 of insert 130. The first end 220 can include a rounded or chamfered blunt distal tip 222 such that it can be placed against surrounding tissue during a suction procedure without cutting or damaging such tissue.

With particular reference to FIGS. 4 and 5, sleeve 190 can include a plurality of flattened sections 206 configured to facilitate receiving and supporting the tracking sensor arrangement 118, as will be described herein. In one exemplary configuration, sleeve 190 can include at least three flattened sections 206 configured to attachably receive tracking device 84. In this configuration, the tracking device 84 can include three coil assemblies 214, as will be described herein. Briefly, in one exemplary configuration, the three coil assemblies 214 can each include a cylindrical configuration as shown in FIGS. 4 and 5, having an overall axial length of approximately 1.5 mm to 2 mm, an overall diameter of approximately 0.3 to 0.5 mm, and a plurality of wire windings wound along a cylindrical base to form the cylindrical configuration. The plurality of windings can form the coil assembly 214 having the generally uniform cylindrical configuration, as generally shown in FIG. 5. Each flattened section 206 can include a slot or depression 218 formed therein and configured to receive a corresponding coil assembly 214, as shown for example in FIGS. 5 and 6. Each slot 218 can be formed in the corresponding flattened section 206 at a 0 to 90 degree angle to a longitudinal axis 208 of the tube assembly 110. In one exemplary configuration, each slot 218 can be formed at a 45 or 55 degree angle to longitudinal axis 208, as shown in FIG. 5. Each of the three flattened sections 206 can be positioned equidistantly or 120 degrees around a circumference of sleeve 190 so that the three coil assemblies 214 are therefore likewise positioned equidistantly around the circumference of sleeve 90, as also generally shown in FIGS. 4-6. It should be appreciated that the coil assemblies can also be coupled to the sleeve without the flattened sections 206, and can be aligned at different orientations relative to the longitudinal axis, including parallel thereto. In this regard, the sleeve 190 can include an outer surface with a circular shape in cross-section configured to receive the coil assemblies 214.

The coil assemblies 214 can include three coil assemblies as described above that cooperate with the navigation system 10 such that 6 DOF tracking information can be determined. It should be appreciated, however, that two coil assemblies 214 could also be used in conjunction with navigation system 10 such that 6 DOF tracking information can also be determined. In a configuration where three coil assemblies 214 are utilized, two of the three coil assemblies can be positioned at an angle relative to the longitudinal axis 208 with the third coil assembly being positioned at an angle relative to the longitudinal axis 208 or parallel thereto. The three coil assemblies 214 can also each be positioned at an angle relative to each other. As discussed above, an exemplary angle of the three coil assemblies 214 relative to the longitudinal axis 208 can be 45 or 55 degrees, which also provides for optimal packaging and spacing of the coil assemblies circumferentially around sleeve 190. It should be appreciated that while an angle of 45 or 55 degrees has been discussed, other angles could be utilized with coil assemblies 214 and instrument 100 as may be required. It should also be appreciated, as discussed above, that the coil assemblies could be positioned parallel or perpendicular to the longitudinal axis 208.

In a configuration where tracking device 84 includes two coil assemblies 214, the two coil assemblies can similarly be positioned equidistant or 180 degrees spaced around an outer perimeter of sleeve 190, as well as can each be positioned at an angle relative to each other and at an angle relative to the longitudinal axis 208 of the tube assembly 110. In this configuration, the two coil assemblies can also cooperate with navigation system 10 such that 6 DOF tracking information can be determined. In one exemplary configuration, the two coil assemblies 214 can be positioned at an angle of about 0 to 90 degrees, including about 45 degrees relative to longitudinal axis 208 of the tube assembly 210.

Figure 8:
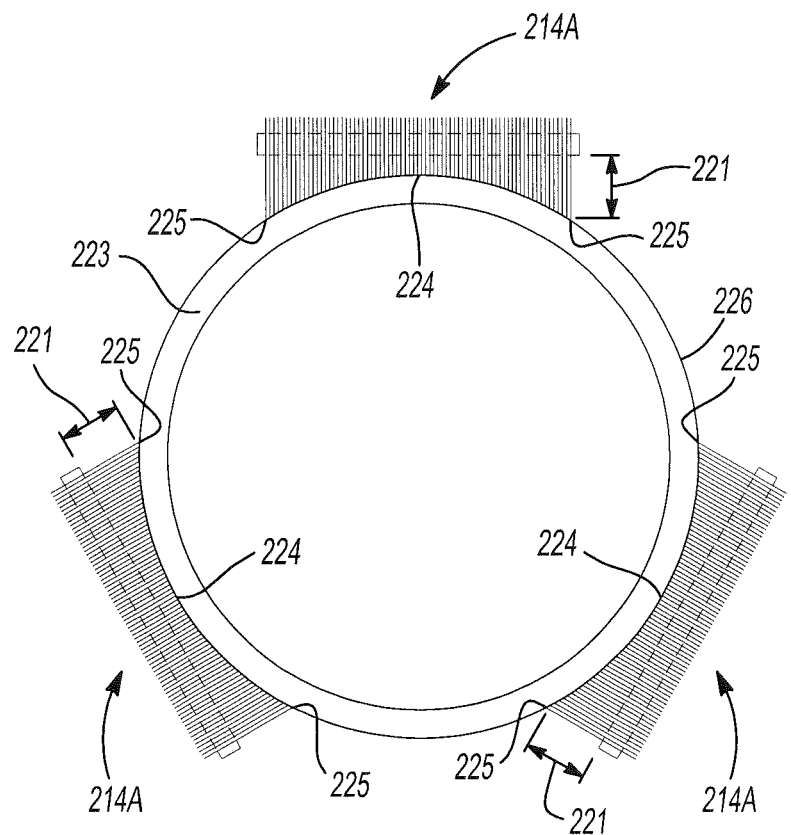
FIGS. 8 and 9 illustrate views of exemplary alternative tracking sensor configurations according to the principles of the present disclosure.
Figure 9:
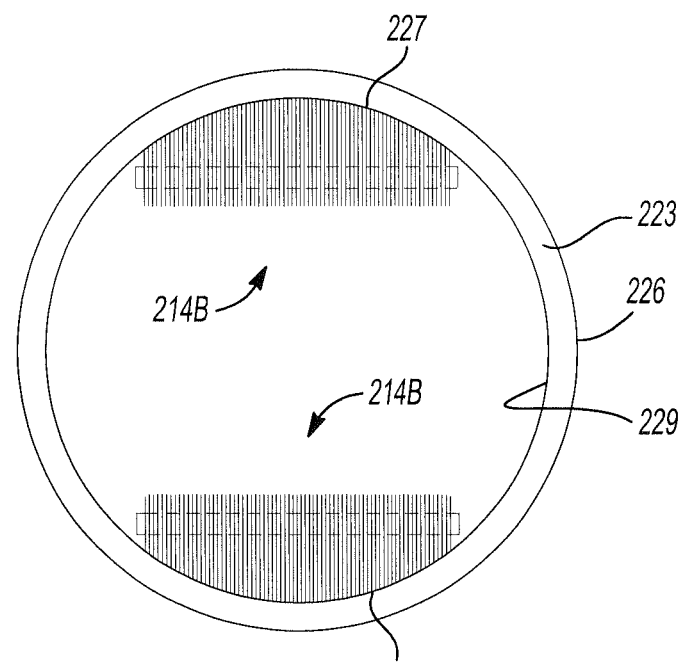

With additional reference to FIGS. 8 and 9, two exemplary coil assemblies 214A and 214B having alternative winding configurations are illustrated operatively associated with an exemplary tubular structure 223 of an exemplary instrument. Coil assemblies 214A and 214B can each include an overall non-linear shape as compared to the overall cylindrical configuration of coils assemblies 214 shown in FIG. 5. Coil assembly 214A can include a central arcuate depression or concavity 224 such that the depression 224 has a smaller outer diameter than opposed ends 225 of the plurality of windings, as generally shown in FIG. 8. The winding configuration of coil assembly 214A can provide an ability to maximize an amount of coil windings on a base wire while working towards minimizing an overall outer dimension or size of an instrument. In this regard, coil assembly 214A is shown in FIG. 8 with the arcuate depression 224 substantially conforming to an outer surface 226 of the tubular structure 223 such that the coil assembly or assemblies 214A essentially nest around the outer surface 226 of the tubular structure. In this regard, because of the general clearance provided by a cylindrical coil assembly positioned adjacent to an outer diameter of the tubular structure 223, a gap or space 221 on either end of the coil can include additional windings without effectively increasing the overall outer diameter of the entire assembly. This can allow for greater or stronger sensitivity in the navigated space.

With particular reference to FIG. 9, coil assembly 214B can include an overall arcuate convex shape 227 configured to conform to and nest within an inner diameter 229 of the exemplary tubular structure. Similar to coil assembly 214A, such a configuration can provide for maximizing an amount of windings on the base wire while also working towards minimizing the inner diameter 229 of the tubular structure 223 that would be required to receive one or more coil assemblies 214B.

Figure 5A:
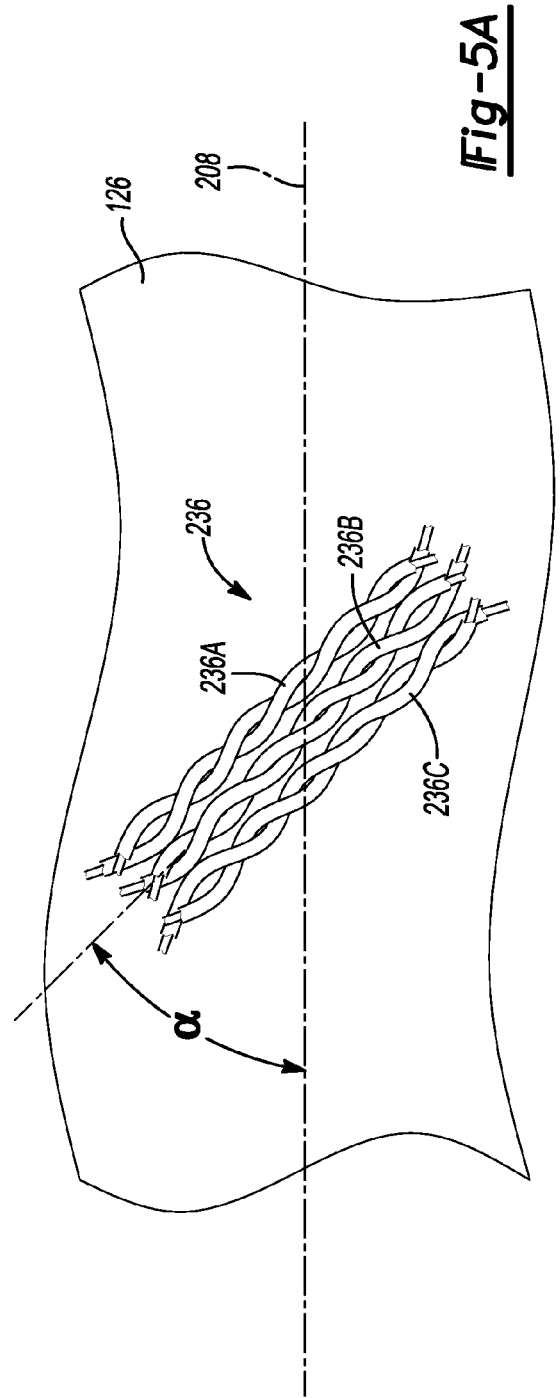
FIG. 5A is an exploded view of an exemplary wire routing configuration according to the principles of the present disclosure.

With particular reference to FIGS. 5 and 5A, the tracking sensor arrangement 118 will now be described in detail. Tracking sensor arrangement 118 can include the tracking device 84 having the two or three coil assemblies 214, as well as a first set of lead wires 228, a printed circuit board 232 and a second set of lead wires 236. The first set of lead wires 228 can include a pair of lead wires 228A for each coil assembly 214, as generally shown in FIG. 6. Each respective pair of lead wires 218A can be routed to a first end of a respective pair of connections 240 on printed circuit board 232. It should be appreciated that while tracking device 84 is described as having three coil assemblies, more or less coil assemblies can be utilized as may be desired or required depending on, for example, characteristics of the navigation system being utilized as well as the number of degrees of freedom desired.

Printed circuit board 232 can include a flexible backing 244 such that it can readily conform to the contour of an outer surface of the body 126, as shown for example in FIG. 4. The flexible printed circuit board 232 can wrap entirely or partially around a perimeter of the body 126 and can be positioned adjacent the second end 148 of body 126, as generally shown in FIGS. 5 and 6. In this manner, the insert portion 130, in its inserted position shown in FIG. 6, can be under all or substantially all of the printed circuit board 232. The rigid insert portion 130 can thus prevent the malleable body 126 from bending or flexing in a region of the printed circuit board 232. In one exemplary configuration, the printed circuit board can be an integral part of sleeve 190.

The second set of lead wires can include three respective pairs of wires 236A, 236B, 236C, as generally shown in FIG. 5 with reference to the partial exploded view in FIG. 5A. It should be appreciated that while FIGS. 2-5, 6-7 and 10 show the second set of lead wires 236 as one element, this is for illustration purposes only and it should be understood that the second set of lead wires shown in FIGS. 2-5, 6-7 and 10 include the three respective pairs of lead wires 236A-C, as shown in FIG. 5A. Each pair of lead wires 236A-C can be twisted together and positioned adjacent each other, as also shown in FIG. 5A. The twisted pairs 236A-C of wires can reduce electrical interference or cross-talk between each pair of adjacent lead wires. Each pair of lead wires can be connected to a single coil assembly 214. The lead wires can also include a Teflon coating or other appropriate lubricous or friction reducing coating on an outer surface thereof. Each pair of lead wires 236A-C can be coupled to an opposite end of respective connectors 240 on printed circuit board 232. It should be appreciated that the lead wires 228 could alternatively extend up the body 126 as a twisted pair of lead wires without the use of printed circuit board 232, or could extend up to and be terminated directly to the respective twisted pair of lead wires 236.

The second set of lead wires 236, which includes the three pairs of twisted wires 236A-C, can be helically wound around elongated body 126 from the printed circuit board 232 to the second end 148, as generally shown for example in FIGS. 3-5A. The wires 236 can be wound around the outside of body 126 at an angle α relative to the longitudinal axis 208 of approximately 0 to 85 degrees, including about 30 degrees, as generally shown in FIGS. 5 and 5A. Each revolution of the wires 236 around body 126 can be spaced apart from each other by a distance D of approximately 2 to 45 mm, including about 5 mm, as shown with reference to FIG. 5. In one exemplary configuration, the range can include from about 15-45 mm. The helical winding of the wires 236 at an acute angle relative to the longitudinal axis along with the relatively close spacing of the wires and the Teflon coating facilitate being able to bend the malleable body 126 at significant angles, including beyond ninety degrees, without breaking or otherwise damaging the wires 236, as will be discussed herein. It should be appreciated that the wires 236 can also be positioned along body 126 in a single revolution from the printed circuit board 232 or the tracking device 84 to the second end 148. In this regard, the revolution spacing can be from about 2 mm to a length of the body 126. The wires 236 can also be positioned along body 126 from the printed circuit board 232 to the second end 148 without being wound around body 136.

Once the second set of wires 236 has been helically wound around the outside of tubular body 126 to the first end 142, the wires can be routed into slots 254 in handle assembly 114 and connected to respective lead wires of a cable connector assembly 258, as generally shown in FIG. 7. The cable connector assembly 258 can be connected to the navigation probe interface 80, as generally shown in FIG. 1. The handle assemble 114 can include two half sections 264, with one half section being shown in FIG. 7 for illustration purposes.

With particular reference to FIG. 6 and continued reference to FIGS. 2-5A, 7 and 10, the tube assembly 110 can include a polymeric outer heat shrink 272 covering the entire assembly, as shown in the cross-sectional view of FIG. 6. Thus, the heat shrink 272 can cover the elongated body 126, the insert portion 130, and the sensor arrangement 118 including the wires helically wound along the body 126. The heat shrink 272 can provide an outer covering or shell over the tube assembly 110 and sensor arrangement 118 while providing sufficient flexibility for both bending of the body 126 and slight relative movement of the helically wound wires 236 as a result of the bending. In this regard, the wires can be moveably captured between the heat shrink and the tubular body. The heat shrink covering can also serve as an electric isolation barrier. It should be appreciated that while the heat shrink covering is only shown in FIG. 6, it has not been shown in the other various views for clarification purposes only to better illustrate the sensor arrangement 118 and routing of wires 236. In this regard, it should be understood that the heat shrink 272 can cover the tube assembly 110 and sensor arrangement 118 shown in FIGS. 2-10.

As discussed above, the handle assembly 114 can include multiple components, such as for example two halves, with one of the halves shown in FIG. 7 receiving the first end of the suction tube assembly 110 in fluid communication with a suction passage 280 formed therein. The suction passage 280 can terminate at a connector 284 protruding from a proximal end of the handle (FIGS. 2 and 3) and can be configured to receive a suction hose or other arrangement in fluid communication with a suction source (not shown). Once the wires are connected to the cable assembly and routed in the slots 254 as discussed above, the other half of handle assembly 114 can connected and an adhesive can be used to bond the handle halves together to form the handle as shown in FIGS. 2 and 3.

With particular reference to FIG. 2, handle assembly 114 can include a suction adjustment feature 290 which can be in the form of a bore 292 extending from an outer surface 294 of the handle assembly 114 and into fluid communication with the suction passage 280. In operation, a surgeon or user 50 of the instrument 100 can place their thumb or another object over the bore 292 to vary an opening of the bore 292 and thus vary an amount of suction pressure realized in the flow path or passage 166. For example, if the bore 292 is left completely open or uncovered, a majority if not all of the suction will be through the bore 292 and not the first end 172 of insert portion 130. On the other hand, if the bore 192 is completely covered or closed off, a maximum amount of suction will be realized at end 172. Varying the opening of bore 292 between fully closed and fully opened can therefore correspondingly vary an amount of realized suction at end 172.

Figure 10:
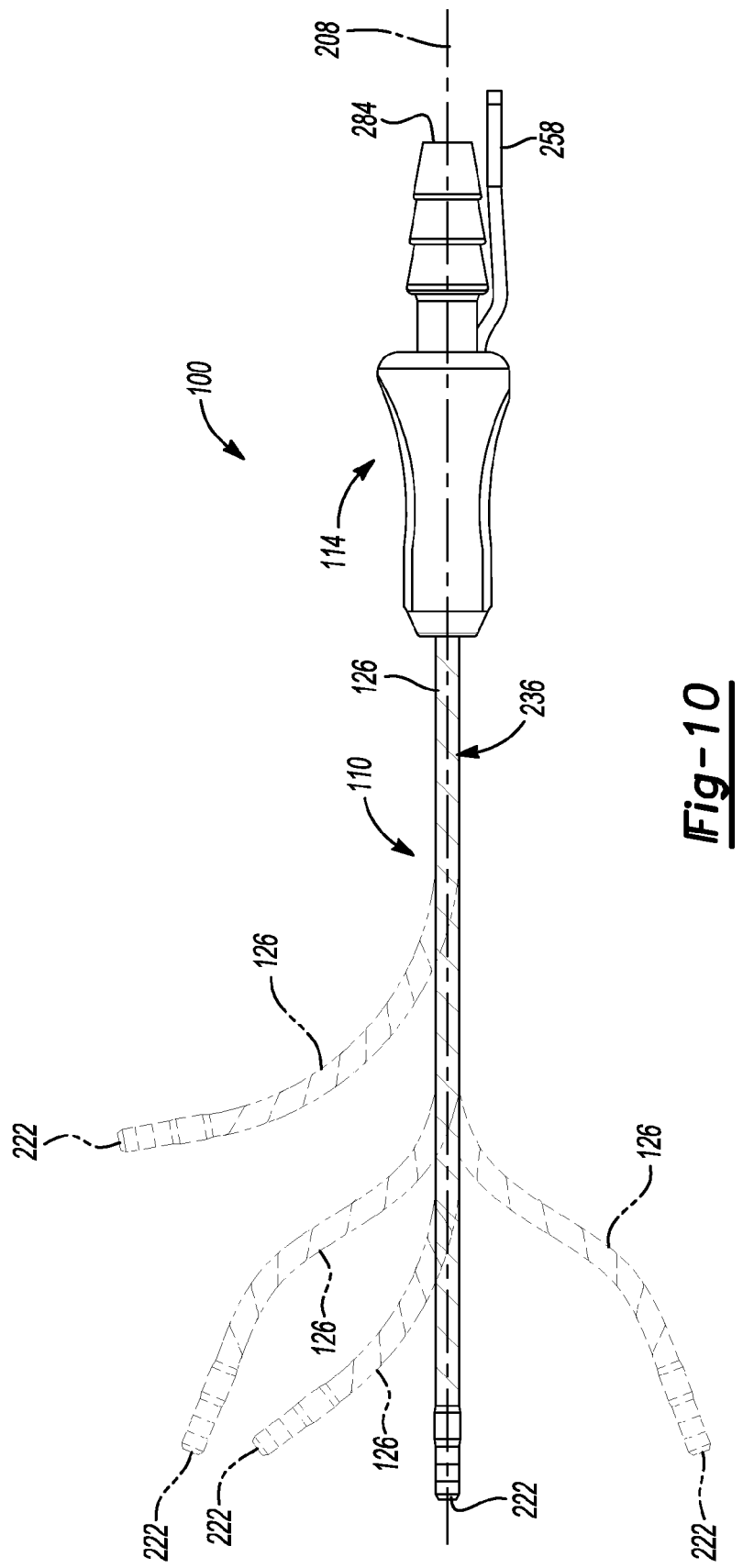
FIG. 10 is a view of exemplary bent or formed configurations of the exemplary malleable suction instrument according to the principles of the present disclosure.

In operation and with additional reference to FIG. 10, the malleable elongated body 126 can be bent into various configurations, as generally shown by the exemplary configurations 300A-D. The malleable nature of body 126 can provide the ability for body 126 to be bent into such various configurations without kinking and can maintain the various configurations until bent or shaped into another configuration. Further, malleable body 126 can be bent or shaped as discussed above without require additional tools, such as a mandrel to facilitate the bending. This is advantageous, for example, in that a surgeon can bend body 126 multiple times by hand during a procedure in close proximity to the patient without having to resort to additional tools or other equipment to facilitate the bending while performing the procedure.

Moreover, the helically wound configuration of wires 236 along with the Teflon coating provides for the ability to bend malleable body 126 at various angles including through ninety degrees without breaking the wires. More specifically, by winding wires 236 helically around body 126 at an angle relative to the longitudinal axis and at a close proximity to each other, the wound wires can conform to the bent shape and move or flex axially with the bent tube such that they do not strain and/or break during the bending. In addition, the Teflon coating provides added lubricity for the wires to have relative motion between the tube and the outer shrink coating 272 during bending.

Further, by providing the tracking device 84 near the distal tip 222, the distal tip 222 of the suction instrument can be tracked to provide substantially accurate position data for the distal tip of suction instrument 100 when out of a line of sight in a body cavity of patient 34. This is particularly useful for the malleable suction instrument 100 because, for example, the tip can be bent or moved relative to the handle and still be tracked. On the other hand, if the tracking device was in the handle (such as in a hind tracked system) and the body 126 was subsequently bent or shaped, the navigation system would no longer be able to accurately track the position of the distal tip. In this regard, the present teaching provide a tip tracked malleable suction instrument that can be bent or shaped into various configurations as may be required during a procedure, and the distal tip can be accurately tracked in any of the various bent positions.

In use, the patient 34 can be positioned on an operating table or other appropriate structure and appropriate image data of a patient or navigation space can be obtained, such as an ENT area. The image data can be registered to the navigation space as is known in the art. The surgeon 50 can determine a shape of the malleable suction instrument 100 to reach a target site and bend the suction instrument 100 to the determined shape where instrument 100 retains the bent shape, as discussed above. The bent or shaped surgical instrument 100 can then be guided to the target site with an icon representing the position of the distal tip of instrument 100 being superimposed on the image data. The icon can show the tracked relative position of the distal tip as instrument 100 is navigated to the target site. In addition, if during navigation of the shaped instrument 100 to the target site, the surgeon determines that the shaped configuration will need to be altered, the surgeon can bend and/or reshape the instrument 100 to a newly shaped configuration and proceed again as discussed above.

Figure 11:
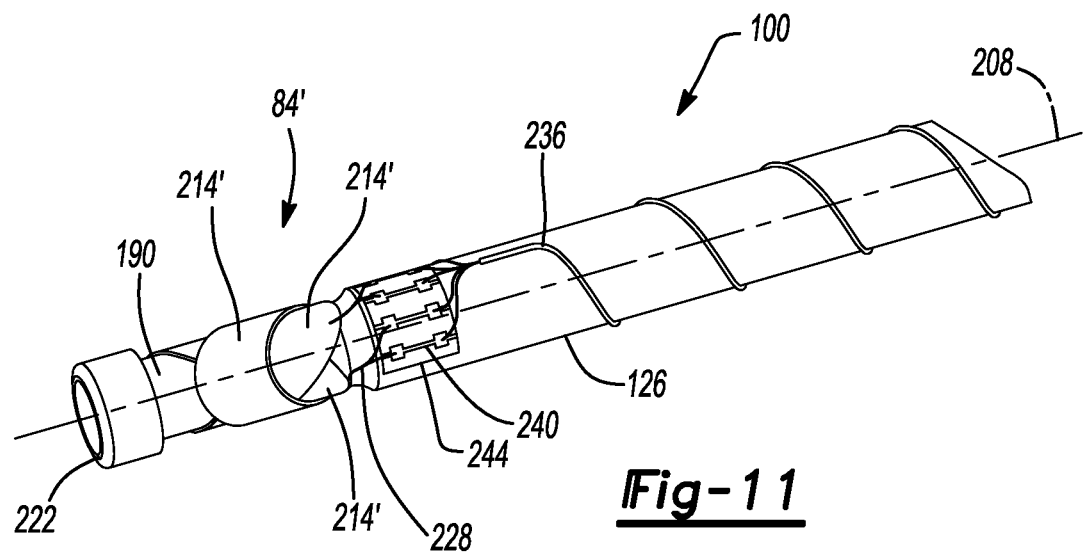
FIG. 11 is a partial perspective view of the distal region of the exemplary suction instrument illustrating an exemplary alternative tracking arrangement according to the principles of the present disclosure.

With additional reference to FIG. 11, an alternative tracking device arrangement 84' will now be discussed. As can be seen in FIG. 11, tracking device 84' can include two or three wrapped coil assemblies 214' that can be used in place of the coil assemblies 214. Coil assemblies 214' can be wrapped around sleeve 190 proximate the distal tip 222. In one exemplary configuration, the coil assemblies 214' can be individually wrapped around sleeve 190 in an overlapping manner with a wrap axis having a non-normal and non-parallel angle to longitudinal axis 208. In the exemplary configuration illustrated, coil assemblies 214' can be wrapped around sleeve 190 at an angle relative to each other and longitudinal axis 208. In another exemplary configuration, coil assemblies 214' can be wrapped around sleeve 190 and spaced axially apart from each other. A further discussion of the coil assemblies 214' can be found in U.S. application Ser. No. 12/770,181, filed on Apr. 29, 2010 and entitled "Method and Apparatus for Surgical Navigation", the disclosure of which is incorporated by reference herein in its entirety.

Figure 12:
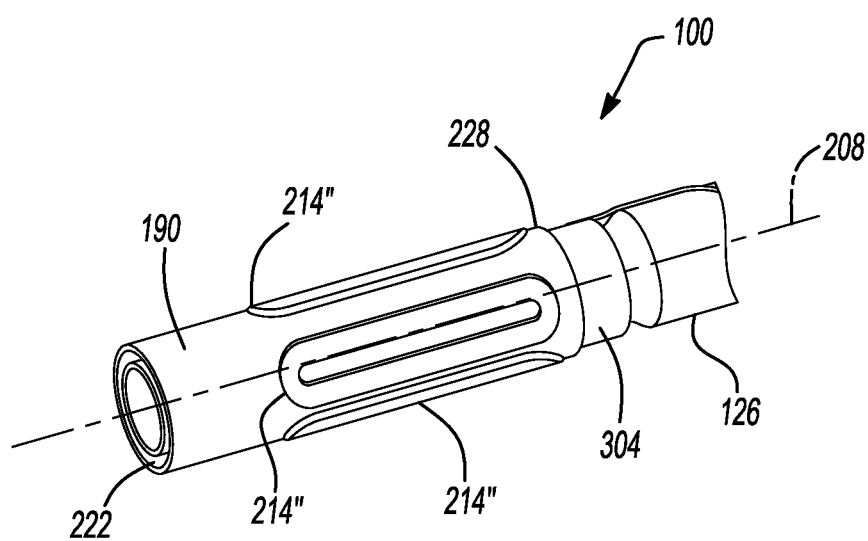
FIG. 12 is a partial perspective view of the distal region of the exemplary suction instrument illustrating another exemplary alternative tracking arrangement according to the principles of the present disclosure.

With additional reference to FIG. 12, another alternative tracking device arrangement 84" is shown associated with instrument 100. Tracking device 84" can also be used in place of tracking device 84 and can include a plurality of oval coil assemblies 214" positioned about sleeve 190 proximate distal tip 222. In one exemplary configuration, two to four coil assemblies 214" can be positioned about sleeve 190 proximate distal tip 222. In the exemplary configuration illustrated, four coil assemblies 214" can be circumferentially spaced around sleeve 190 proximate distal tip 222, and an axial coil 304 can be positioned proximally of coil assemblies 214", as shown in FIG. 12. In one exemplary configuration, two oval coil assemblies 214" can be provided with the axial coil 304. The two coil assemblies 214" can also include two pair of coil assemblies 214" provided with the axial coil 304.

The coil assemblies 214" can be formed in various selected shapes, such as elliptical, circular, or oval. In one exemplary configuration, the axial coil 304 can be concentric with and wrapped around an outer surface of sleeve 190 or body 126, as shown in FIG. 12. A further discussion of coil assemblies 214" and axial coil 304 can be found in U.S. application Ser. No. 13/016,740, filed on Jan. 28, 2011 and entitled "Method and Apparatus for Image-Based Navigation", the disclosure of which is incorporated by reference herein in its entirety.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A surgical instrument, comprising:
   a body having a proximal end and a distal end, wherein the body is tubular-shaped and has a first internal flow channel extending between the proximal end and the distal end;
   a sleeve distal to the body and having a proximal end and a distal end, wherein the proximal end of the sleeve is adjacent to and not in contact with the distal end of the body;
   a tracking assembly adapted to cooperate with a navigation system to track a distal tip of the instrument, wherein the tracking assembly comprises a printed circuit board and a plurality of coils including a first coil, wherein each of the plurality of coils is wrapped around a respective one of a plurality of cores, and wherein the first coil is mounted on the sleeve;
   a handle coupled to the proximal end of the body, wherein the handle comprises a second internal flow channel in fluid communication with the first internal flow channel;
   a first pair of lead wires wound around the body from the tracking assembly to the handle;
   a set of wires connecting the printed circuit board to the first coil, wherein the printed circuit board connects the first pair of lead wires to the set of wires; and
   an insert received in the sleeve and the distal end of the body, wherein the insert is straight and tubular-shaped, wherein the insert is under at least a portion of the printed circuit board and prevents bending or flexing in a region of the printed circuit board, and
   wherein the insert provides rigid support for the sleeve and the distal end of the body, maintains alignment of the sleeve relative to the distal end of the body, and prevents bending of the sleeve and the distal end of the body.

2. The surgical instrument of claim 1, wherein the first pair of lead wires is helically wound around the body from the tracking assembly to the handle.

3. The surgical instrument of claim 2, wherein the first pair of lead wires are helically wound around the body with consecutive revolutions of the first pair of lead wires being axially spaced apart by 15-45 mm.

4. The surgical instrument of claim 3, further comprising a shrink fit layer covering the body, the tracking assembly, and the sleeve.

5. The surgical instrument of claim 3, wherein the first pair of lead wires are twisted together and helically wound around the body at an angle of 5-45 degrees relative to a longitudinal axis of the body.

6. The surgical instrument of claim 2, wherein the first pair of lead wires comprises a lubricous coating.

7. The surgical instrument of claim 1, wherein:
   the sleeve includes a depression;
   the depression has a longitudinal axis positioned at an acute angle relative to a longitudinal axis of the body; and
   the depression is configured to receive the first coil.

8. The surgical instrument of claim 7, wherein the acute angle is 55 degrees.

9. The surgical instrument of claim 1, wherein:
   the sleeve includes a plurality of depressions equally spaced circumferentially around an outer surface of the sleeve;
   each of the plurality of depressions has a longitudinal axis positioned at a respective acute angle relative to a longitudinal axis of the body;
   the plurality of coils comprises the first coil, a second coil, and a third coil; and
   each of the plurality of coils is disposed in a respective one of the plurality of depressions.

10. The surgical instrument of claim 9, wherein:
    the sleeve further includes a plurality of planar sections spaced circumferentially around the outer surface of the sleeve; and
    each of the plurality of depressions is formed in a corresponding one of the plurality of planar sections.

11. The surgical instrument of claim 9, wherein:
    the tracking assembly comprises a plurality of pairs of lead wires extending between the handle and the printed circuit board;
    the printed circuit board is mounted on the distal end of the body;

the first coil corresponds to the first pair of lead wires;
the second coil corresponds to a second pair of lead wires;
the third coil corresponds to a third pair of lead wires;
the plurality of pairs of lead wires comprise the first pair of lead wires, the second pair of lead wires, and the third pair of lead wires; and
each of the plurality of pairs of lead wires is helically wound around the body and adjacent to each other from the tracking assembly to the handle with consecutive revolutions of the plurality of pairs of lead wires being axially spaced apart by approximately 15-45 mm.

12. The surgical instrument of claim 11, further comprising a shrink layer covering the sleeve, the insert, the circuit board, and the body, wherein the plurality of pairs of lead wires are moveably captured between the shrink layer and the body.

13. The surgical instrument of claim 1, wherein:
the first coil is cylindrically-shaped and has a plurality of windings; and
the plurality of windings have an outer diameter of less than 0.5 mm and an axial length of 1.5-2.0 mm.

14. The surgical instrument of claim 1, wherein:
the first coil has a plurality of windings wound to form at least a partially concave outer surface between opposed ends of the coil; and
the concave outer surface is configured to nest around a cylindrical surface of the sleeve.

15. The surgical instrument of claim 1, wherein:
the tracking assembly includes a second coil adjacent to the distal end of the body; and
the first coil and the second coil are orientated perpendicular to a longitudinal axis of the body.

16. The surgical instrument of claim 1, wherein:
the tracking assembly includes a second coil; and
the first coil and the second coil are individually wrapped around the body adjacent a distal tip of the sleeve and at an acute angle relative to a longitudinal axis of the body.

17. The surgical instrument of claim 16, wherein:
the tracking assembly includes a third coil; and
the first coil, the second coil, and the third coil are individually wrapped around the body and overlap one another.

18. The surgical instrument of claim 1, wherein:
the first coil is an axial coil; and
the tracking assembly includes two oval-shaped coils adjacent a distal tip of the sleeve.

19. The surgical instrument of claim 1, wherein:
the body is formed from a malleable metallic material such that the body can be bent without kinking from a first configuration to a second configuration;
the body is configured to maintain the second configuration until being manually bent from the second configuration to a third configuration; and
the pair of lead wires is configured to conform to the body during bending of the body.

20. The surgical instrument of claim 1, wherein:
the body comprises (i) a first inner diameter, and (ii) a second inner diameter at the distal end of the body;
the first inner diameter is smaller than the second inner diameter;
the sleeve comprises a third inner diameter, wherein the third inner diameter matches the second inner diameter; and
the insert comprises an outer diameter; and
the outer diameter is substantially equal to the second inner diameter and the third inner diameter.

21. The surgical instrument of claim 1, wherein:
the printed circuit board is on the distal end of the body and comprises connectors;
the first pair of lead wires is connected to the connectors; and
the set of wires extend from the connectors to the first coil and over a gap between the sleeve and the distal end of the body.

22. The surgical instrument of claim 1, further comprising a plurality of pairs of lead wires, wherein:
the tracking assembly comprises a plurality of coils;
the plurality of coils comprise the first coil and a second coil;
the plurality of pairs of lead wires helically wrap around the body from the handle to the distal end of the body; and
each of the pairs of lead wires is connected to a respective one of the plurality of coils.

23. The surgical instrument of claim 1, wherein the tracking assembly comprises:
a plurality of connectors mounted on the distal end of the body; and
the set of wires extending between the plurality of connectors and the first coil.

24. A surgical instrument, comprising:
a body having a proximal end and a distal end, wherein the body is tubular shaped and has a first internal flow channel extending between the proximal end and the distal end;
an insert having a proximal end, wherein the insert is straight and tubular-shaped, and wherein the proximal end of the insert is configured to be received in the distal end of the body;
a sleeve configured to slide over the insert;
a tracking assembly comprising a plurality of connectors, a first set of wires, and a plurality of coils, wherein the plurality of connectors are mounted on the distal end of the body, wherein the first set of wires extends from the plurality of connectors to the plurality of coils, wherein the plurality of coils are mounted on the sleeve, wherein each of the plurality of coils is wrapped around a respective one of a plurality of cores, and wherein the tracking assembly is adapted to cooperate with a navigation system to track a distal tip of the instrument;
a handle coupled to the proximal end of the body and including a second internal flow channel in fluid communication with the first internal flow channel;
a second set of wires helically wound around the body from the handle to the distal end of the body and at an acute angle relative to a longitudinal axis of the body,
wherein the plurality of connectors connect the first set of wires to the second set of wires, and
wherein the insert is under at least a portion of plurality of connectors and prevents bending or flexing in a region of the plurality of the connectors; and
an outer layer covering the body, the sleeve, the insert and the tracking assembly.

25. The surgical instrument of claim 24, wherein:
each of the plurality of coils includes a longitudinal axis orientated at an acute angle relative to the longitudinal axis of the body; and
the plurality of coils are rigidly supported by the insert.

26. The surgical instrument of claim 24, wherein the plurality of coils are orientated at (i) acute angles relative to the longitudinal axis of the body, and (ii) acute angles relative to each other.

27. The surgical instrument of claim 26, wherein each of the plurality of coils is positioned equidistant from each other around a circumference of the sleeve.

28. The surgical instrument of claim 24, wherein each of the plurality of coils includes a longitudinal axis orientated perpendicular to the longitudinal axis of the body.

29. The surgical instrument of claim 24, further comprising (i) a first plurality of sets of wires connecting the plurality of connectors to the plurality of coils, and (ii) a second plurality of sets of wires extending from the handle to the plurality of connectors, wherein:
- the first plurality of sets of wires comprise the first set of wires;
- the second plurality of sets of wires comprise the second set of wires;
- the tracking assembly comprises a printed circuit board;
- the printed circuit board comprises the plurality of connectors;
- each of the plurality of coils corresponds to one of the first plurality of sets of wires and one of the second plurality of sets of wires; and
- the second plurality of sets of wires are helically wound adjacent to each other and around the body at an acute angle relative to the longitudinal axis of the body.

30. The surgical instrument of claim 29, the proximal end of the insert extends into the body and through a center opening of the printed circuit board.

31. The surgical instrument of claim 24, wherein a distal tip of the sleeve is chamfered or rounded.

32. The surgical instrument of claim 24, wherein the outer layer comprises a polymeric material and is shrink fit over the body, the sleeve, the insert and the tracking assembly.

33. The surgical instrument of claim 24, wherein the second set of wires are moveably captured between the outer layer and the body.

34. A surgical instrument, comprising:
- a body having a proximal end and a distal end, wherein the body is tubular-shaped and has an inner diameter defining (i) a first internal flow channel between the proximal end and the distal end, and (ii) an annular recess formed in the distal end;
- an insert having a proximal end and a distal tip, wherein the proximal end of the insert is configured to be received in the annular recess of the distal end of the body;
- a sleeve configured to be received over only a portion of the insert and extend from the distal end of the insert towards the proximal end of the insert;
- a tracking assembly coupled to the sleeve and the body, wherein the tracking assembly is adapted to cooperate with a navigation system to track the distal tip of the insert, wherein the tracking assembly includes a printed circuit board and at least two electromagnetic coils, wherein the at least two electromagnetic coils are disposed in respective depressions in an outer surface of the sleeve, wherein each of the at least two electromagnetic coils is positioned at an acute angle relative to a longitudinal axis of the body and wrapped around a respective one of a plurality of cores, and wherein the at least two electromagnetic coils and at least a portion of the printed circuit board are supported by the insert;
- a handle coupled to the proximal end of the body and including a second internal flow channel in fluid communication with the first internal flow channel,
- wherein the tracking assembly includes a pair of lead wires for each of the at least two electromagnetic coils, wherein the pairs of lead wires are helically wound around the body adjacent to each other and at an acute angle relative to the longitudinal axis of the body
- a plurality of wires connecting the at least two electromagnetic coils to the printed circuit board,
- wherein the printed circuit board connects the pairs of lead wires to the plurality of wires, and
- wherein the insert is under at least a portion of the printed circuit board and prevents bending or flexing in a region of the printed circuit board; and
- a heat shrink layer covering the body, the sleeve, the insert and the tracking assembly,
- wherein the pairs of lead wires are moveably captured between the body and the heat shrink layer.

35. The surgical instrument of claim 34, wherein:
- each of the pairs of lead wires is separate from the other pairs of lead wires;
- each of the pairs of lead wires comprises a first wire and a second wire; and
- the second wire of each of the pairs of lead is twisted with the corresponding one of the first wires.

* * * * *